(12) United States Patent
Kubota et al.

(10) Patent No.: US 11,207,052 B2
(45) Date of Patent: Dec. 28, 2021

(54) ULTRASONIC DIAGNOSTIC APPARATUS AND SHIELD STRUCTURE

(71) Applicant: Hitachi, Ltd., Tokyo (JP)

(72) Inventors: Hidenao Kubota, Tokyo (JP); Masaharu Hirata, Tokyo (JP); Yuta Tokita, Tokyo (JP)

(73) Assignee: HITACHI, LTD., Tokyo (JP)

( * ) Notice: Subject to any disclaimer, the term of this patent is extended or adjusted under 35 U.S.C. 154(b) by 79 days.

(21) Appl. No.: 16/737,411

(22) Filed: Jan. 8, 2020

(65) Prior Publication Data

US 2020/0253581 A1 Aug. 13, 2020

(30) Foreign Application Priority Data

Feb. 12, 2019 (JP) .............................. JP2019-022463

(51) Int. Cl.
*H05K 9/00* (2006.01)
*A61B 8/00* (2006.01)

(52) U.S. Cl.
CPC ................ *A61B 8/44* (2013.01); *H05K 9/002* (2013.01); *A61B 8/4405* (2013.01); *A61B 8/4427* (2013.01); *H05K 9/0049* (2013.01)

(58) Field of Classification Search
CPC .................................................... H05K 9/0001
See application file for complete search history.

(56) References Cited

U.S. PATENT DOCUMENTS 5,063,273 A * 11/1991 Bloks .................. H05K 9/0001
174/376

FOREIGN PATENT DOCUMENTS

JP      2001-112751 A    4/2001
JP      2001-212141 A    8/2001

* cited by examiner

*Primary Examiner* — Hung V Ngo
(74) *Attorney, Agent, or Firm* — Foley & Lardner LLP (57) ABSTRACT

To reduce noise which leaks to the outside in an ultrasonic diagnostic apparatus.
An internal AC wiring unit 34 is composed of internal AC wiring which is installed on the input side of a power source circuit, and a shield case 38 which accommodates it. The internal AC wiring includes an inlet, a plurality of connectors, a relay substrate, and a plurality of internal AC cables. The internal AC wiring is protected from radiation noise which is generated in a casing 22 by the shield case 38. Thereby, the noise which leaks to the outside via an external AC cable is reduced.

5 Claims, 6 Drawing Sheets

ULTRASONIC DIAGNOSTIC APPARATUS AND SHIELD STRUCTURE

TECHNICAL FIELD

The present invention relates to an ultrasonic diagnostic apparatus and a shield structure, and, in particular, relates to the shield structure which is installed in an apparatus main body.

BACKGROUND ART

The ultrasonic diagnostic apparatus is a medical apparatus which forms an ultrasonic image on the basis of a reception signal which is obtained by wave transmission and reception of ultrasonic waves to and from a subject. As the ultrasonic diagnostic apparatus, a cart-type ultrasonic diagnostic apparatus, a portable-type ultrasonic diagnostic apparatus and so forth are known. In the following, the cart-type ultrasonic diagnostic apparatus will be taken as an example and a configuration thereof will be described.

The cart-type ultrasonic diagnostic apparatus is, in general, equipped with an apparatus main body, an operation panel, a display and so forth. A plurality of casters are attached to a lower part of the apparatus main body. In addition, a lifting mechanism is installed on the apparatus main body and the operation panel is supported by the lifting mechanism. An arm mechanism is installed on the depth side of the operation panel, and the display is held by the arm mechanism. A boxed-shaped casing is installed in the apparatus main body, and a plurality of substrates are accommodated in the casing. The casing is composed of metal, and it functions, in general, as a housing and a shield case. Incidentally, spaces among the substrates in the casing are becoming narrower and narrower as the apparatus main body is miniaturized. Therefore, electromagnetic waves which are generated in an electronic circuit in the housing become more liable to be trapped therein at a high level.

CITATION LIST

Patent Literature

[Patent Literature 1] Japanese Patent Application Laid-Open No. 2001-212141
[Patent Literature 2] Japanese Patent Application Laid-Open No. 2001-112751 (in particular, FIG. 3 and FIG. 4)

SUMMARY OF INVENTION

Technical Problem

In the casing of the ultrasonic diagnostic apparatus, the electromagnetic waves are radiated from the electronic circuit and a signal line. When noise is induced in internal AC wiring (an internal AC cable and so forth which are installed on the input side of a power source circuit) caused by such electromagnetic waves (can be also called radiation noise), the noise passes through the internal AC cable and an external AC cable and leaks to the outside of the casing. Radiation of the electromagnetic waves from the external AC cable is induced with the leaked-out noise.

An ultrasonic diagnostic apparatus which has the shield case is disclosed in Patent Literature 1. The power source circuit and the AC wiring are accommodated together in the shield case. A configuration which shields the power source circuit and the AC wiring individually is not confirmed in Patent Literature 1. In addition, specific shape and arrangement of the shield case are not described in Patent Literature 1.

An ultrasonic diagnostic apparatus which has a case which accommodates an AC/DC converter and a case which accommodates the AC wiring is disclosed in Latent Literature 2. It is understood that those cases are present on the outer side of the casing, and a configuration which prevents or reduces noise induction in the casing is not confirmed in Patent Literature 2.

An object of the present invention is to suppress the noise which leaks to the outside in an ultrasonic diagnostic apparatus. Otherwise, an object of the present invention is to protect the internal AC wiring from the radiation noise in the ultrasonic diagnostic apparatus.

Solution to Problem

An ultrasonic diagnostic apparatus pertaining to the present invention includes a housing which functions as an outer shield case, a first inner shield case which is installed in the housing and accommodates a power source circuit which supplies power to an electronic circuit which functions in an ultrasonic diagnosis, and a second inner shield case which is a shield case which is different from the first inner shield case, is installed in the housing and accommodates internal AC wiring which is installed on the input side of the power source circuit.

A shield structure pertaining to the present invention includes a first inner shield case which is installed in a housing which functions as an outer shield case and accommodates a power source circuit which supplies power to an electronic circuit which functions in an ultrasonic diagnostic apparatus, and a second inner shield case which is a shield case which is different from the first inner shield case, is installed in the housing and accommodates internal AC wiring which is installed on the input side of the power source circuit.

Advantageous Effects of Invention

According to the present invention, the noise which leaks to the outside can be suppressed. Otherwise, according to the present invention, the internal AC wiring can be protected from the radiation noise.

DESCRIPTION OF EMBODIMENTS

In the following, an embodiment will be described on the basis of the drawings.

(1) Summary of Embodiment

An ultrasonic diagnostic apparatus pertaining to an embodiment has a housing which functions as an outer shield case, a first inner shield case, and a second inner shield case. The first inner shield case is the one which is installed in the housing and accommodates a power source circuit which supplies power to an electronic circuit which functions in an ultrasonic diagnosis. The second inner shield case is the one which is a shield case which is different from the first inner shield case, is installed in the housing and accommodates internal AC wiring which is installed on the input side of the power source circuit.

According to the above-mentioned configuration, since the internal AC wiring is accommodated in the second inner shield case in the housing, the internal AC wiring is protected from radiation noise which is generated in the housing. That is, induction of the noise in the internal AC wiring is suppressed. Thereby, the noise which leaks to the outside can be reduced.

In the housing, the electromagnetic wave, that is, the radiation noise which is generated in the power source circuit is locally trapped inside by the first inner shield case. Thereby, induction of the noise in the electronic circuit and the internal AC wiring which is caused by the radiation noise which is generated in the power source circuit is prevented or reduced. Seeing from such viewpoints as above, special technical significance is recognized in a combination between the first inner shield case and the second inner shield case.

In the embodiment, in the internal AC wiring, a relay substrate, a first internal AC cable which is installed between an external AC cable and the relay substrate and a second internal AC cable which is installed between the relay substrate and the power source circuit are included. A circuit pattern is formed on the relay substrate and there are cases where a relay connector is installed thereon. The relay substrate is also a wiring-densely-crowded part. Viewing from such viewpoints, generally observing, the relay substrate is a component which is susceptible to the radiation noise. According to the above-mentioned configuration, since the relay substrate is accommodated in the second inner shield case, the relay substrate is protected from the radiation noise. In addition, since the first internal AC cable and the second internal AC cable are accommodated in the second inner shield case, they are also protected from the radiation noise. Incidentally, in a case where a main power source switch is installed between the external AC cable and the relay substrate, two internal AC cables are installed as the first internal AC cable.

In the embodiment, in the internal AC wiring, further, a third internal AC cable which is installed between the relay substrate and a power source connector for external equipment is included. According to this configuration, the noise which leaks through the external AC cable to which the external equipment is connected can be effectively suppressed. In a case where a plurality of the external AC cables are connected to the internal AC wiring, a leakage amount of noise becomes liable to increase and therefore the above-mentioned configuration more effectively functions.

In the embodiment, in the internal AC wiring, an internal AC cable which supplies the power to the power source circuit is included, the first inner shield case has a first side face which has a first opening which accepts the internal AC cable, the second inner shield case has a second side face which has a second opening which ejects the internal AC cable, and the first side face and the second side face mutually face. According to this configuration, since a length of the internal AC cable from the internal AC wiring to the power source circuit can be made short, noise induction in the internal AC cable concerned can be reduced.

In the embodiment, the first opening and the second opening are close to each other, and the first opening and the second opening are in a positional relation that they at least partially overlap when viewing from a direction which is orthogonal to the first side face and the second side face. According to this configuration, since an exposed part (a part which is not covered with the two inner shield cases) of the internal AC cable can be made short, the noise induction in the internal AC cable concerned can be more reduced. In general, when a distance between the two openings is not more than 2 cm, it can be said that they are close to each other.

In the embodiment, the housing has a front face plate which is equipped with a probe connector, and a rear face plate. A digital electronic circuit, an analog electronic circuit, the power source circuit, and the internal AC wiring are accommodated in an internal space between the front face plate and the rear face plate. According to this configuration, a space which is surrounded by the rear face plate and the first inner shield case becomes a first shielded chamber, and the power source circuit is arranged in the first shielded chamber. In addition, a space which is surrounded by the rear face plate and the second inner shield case becomes a second shielded chamber, and the internal AC wiring is arranged in the second shielded chamber. According to the above-mentioned configuration, the number of components can be reduced while realizing effective shield.

A shield structure pertaining to the embodiment includes a first inner shield case and a second inner shield case. The first inner case is the one which is installed in a housing which functions as an outer shield case and accommodates a power source circuit which supplies power to an electronic circuit which functions in an ultrasonic diagnosis. The second inner shield case is the one which is a shield case which is different from the first inner shield case, is installed in the housing and accommodates internal AC wiring which is installed on the input side of the power source circuit. Although this shield structure is desirably installed on a rear part of an equipment main body, it may be also installed on a lower part or a side part of the equipment main body.

(2) Details of Embodiment

Figure 1:
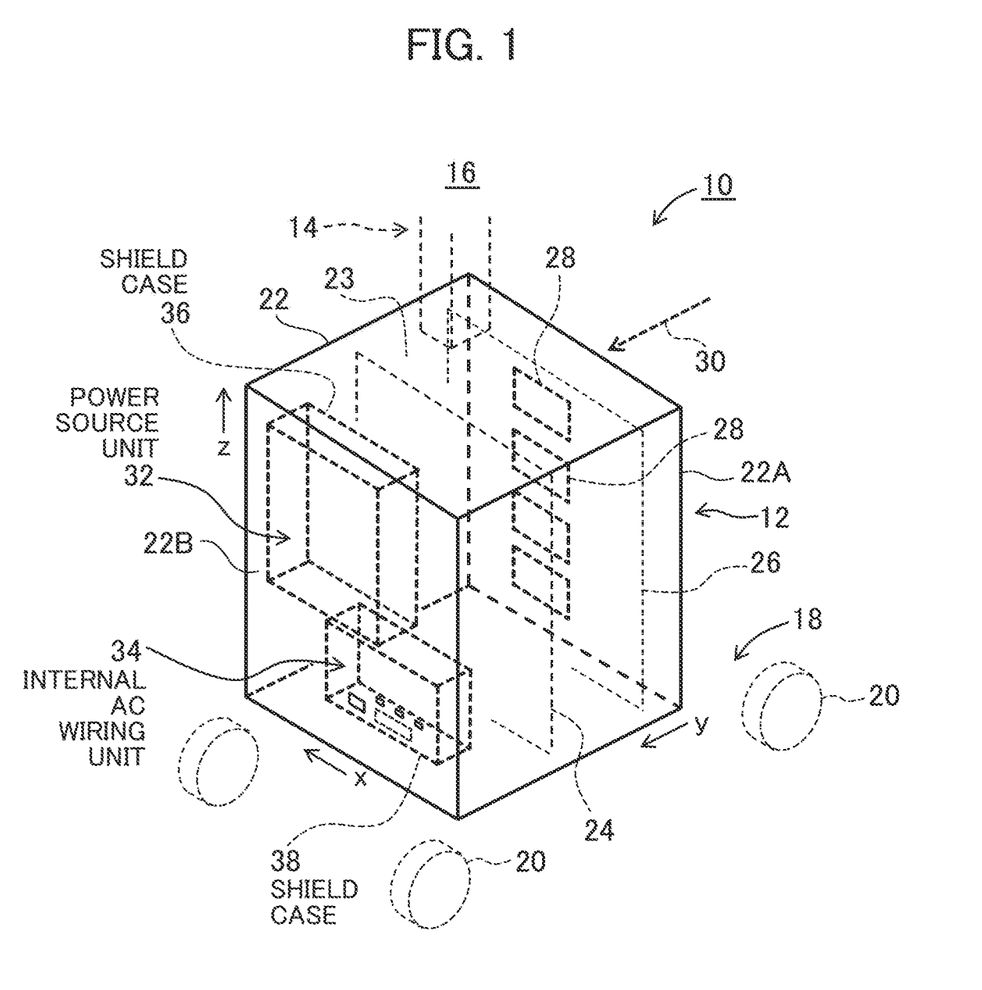
FIG. 1 is a perspective diagram illustrating an ultrasonic diagnostic apparatus pertaining to an embodiment.

The ultrasonic diagnostic apparatus pertaining to the embodiment is illustrated in FIG. 1. The ultrasonic diagnostic apparatus is a medical apparatus which is adapted to diagnose a living body with ultrasonic waves in a medical institution such as a hospital and so forth. In the ultrasonic diagnosis, ultrasonic waves are transmitted to and received from the living body and an ultrasonic image is formed on the basis of a reception signal which is obtained thereby. A tomographic image, a blood flow image, a Doppler image, an elastic information image and so forth are given as the ultrasonic image.

In FIG. 1, an ultrasonic diagnostic apparatus 10 which serves as a cart-type ultrasonic diagnostic apparatus has an apparatus main body, a support mechanism 14, an operation panel 16 and so forth. The support mechanism 14 includes a lifting mechanism, and the operation panel 16 is supported by the lifting mechanism. Illustration of the operation panel 16 is omitted in FIG. 1. The operation panel 16 functions as an input device, and it, specifically, has a plurality of buttons, a plurality of switches, a trackball, a keyboard and so forth. An arm mechanism is installed on the depth side of the operation panel 16 and a display is held by the arm mechanism. In FIG. 1, illustration of the arm mechanism and the display is omitted.

Four casters 20 are installed on a lower part 18 of the apparatus main body 12. Although the lower part 18 has four leg parts to which the four casters 20 are attached, illustration of them is omitted in FIG. 1. Incidentally, in FIG. 1, an x direction is a left-right direction as a first horizontal direction, and a y direction is a depth-wise direction as a second horizontal direction. A z direction is a vertical direction.

The apparatus main body 12 has a box-shaped casing 22. The casing 22 is configured by a metal member, and functions as a housing and a shield case (an outer shield case). The casing 22 has a front face plate 22A and a rear face plate 22B which are arranged side by side in parallel, keeping a fixed distance therebetween in the y direction. The casing 22 has a right side face plate, a left side face plate, an upper face plate, and a lower face plate besides them. Four main body-side connectors 28 are installed on the front face plate 22A in the illustrated configuration example. An ultrasonic probe is detachably connected to each main body-side connector 28.

The ultrasonic probe is configured by a probe head which has an ultrasonic vibrator, a probe-side connector which is mounted onto the main body-side connector 28, and a probe cable which is installed between the probe head and the probe connector. Incidentally, the casing 22 is covered with a not illustrated decorative panel. The decorative panel is composed of, for example, resin.

A plurality of circuits, a plurality of cables, a plurality of pieces of equipment and so forth are installed in an inner space 23 that the casing 22 has as a plurality of electronic components adapted to perform the ultrasonic diagnosis. In FIG. 1, two substrates 24, 26 are illustrated by way of example. For example, a transmission circuit, a reception circuit and so forth are installed on the substrate 26. They are configured as, for example, analog electronic circuits. A clock generator, a CPU, a memory, a hard disk, a controller and so forth are installed on the substrate 24. They are digital electronic circuits or digital devices.

Electromagnetic waves (radiation noise) are generated from the plurality of digital electronic circuits and the plurality of analog electronic circuits in the casing 22. For example, also a basic clock line could become a noise source. Although the electromagnetic waves which are generated in the respective electronic circuits are basically trapped in the casing 22 which acts as a shield case, when noise is generated in the internal AC wiring due to that, the noise leaks out of the internal AC wiring to the outside through the external AC cable which is connected thereto. In the embodiment, in order to prevent such noise leakage, a special shield structure is installed in the casing 22. In the following, description will be made about it in detail.

A power source unit 32 and an internal AC wiring unit 34 are installed on an inner face (a face which faces the internal space 23) of the rear face plate 22B. The power source unit 32 is configured by the power source circuit, and a shield case (a first inner shield case) 36 which accommodates it. The power source circuit is an AC (Alternate Current)/DC (Direct Current) conversion circuit. The power source circuit generates, in general, a plurality of DC voltages. The power source circuit is configured as, for example, a switching power source circuit. The power source circuit is installed in the shild case 36 such that the electromagnetic waves which are generated in the power source circuit would not diffuse in the casing 22.

The shield case 36 is configured by a box-shaped metal member. Specifically, in the illustrated configuration example, the shield case 36 is configured by a front face plate, a right side face plate, a left side face plate, an upper face plate, and a lower face plate. A space which is surrounded by the shield case 36 and the rear face plate of the casing 22 becomes a shielded chamber. The power source circuit is installed in the shielded chamber. The shield case 36 is fixed to the rear face plate 22B with a plurality of screws. A rear face plate may be further added to the shield case 36 itself.

The internal AC wiring unit 34 is configured by internal AC wiring, and a shield case (a second inner shield case) 38 which accommodates it. The AC internal wiring corresponds to a component group or a wiring organization which is installed on the input side of the power source circuit, and a plurality of internal AC cables, a relay substrate with connectors, a plurality of connectors, an inlet and so forth are included therein. A plug which configures an end of the external AC cable is inserted into the inlet. The power from the outside is supplied thereto. The plurality of connectors are used as necessary, and a plurality of the external AC cables which are connected to a plurality of pieces of optional equipment are connected thereto.

The shield case 38 is configured by a box-shaped metal member. Specifically, in the illustrated configuration example, the shield case 38 is configured by a front face plate, a right side face plate, a left side face plate, an upper face plate, and a lower face plate similarly to the above-mentioned shield case 36. A space which is surrounded by the shield case 38 and the rear face plate 22B of the casing 22 becomes a shielded chamber. The internal AC wiring is installed in the shielded chamber. The shield case 38 is fixed to the rear face plate 22B with a plurality of screws. A rear face plate may be further added to the shield case 36 itself.

Figure 2:
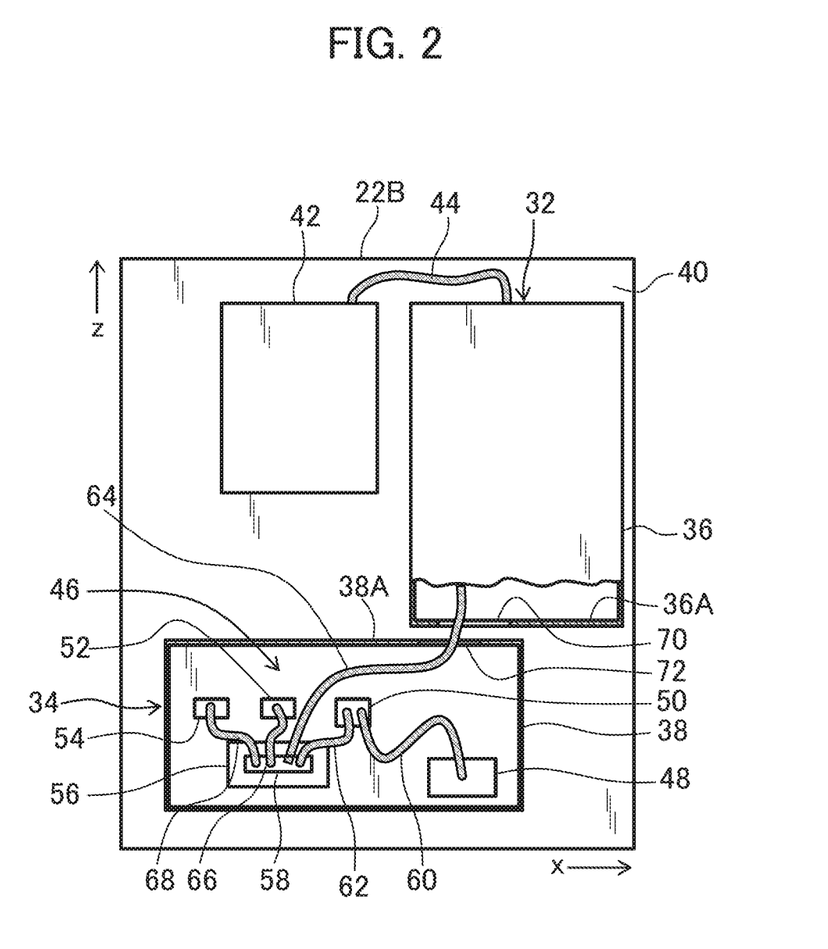
FIG. 2 is a schematic diagram illustrating a first practical example of a shield structure.

A first practical example of the shield structure pertaining to the embodiment is illustrated in FIG. 2. As already described, the power source unit 32 and the internal AC wiring unit 34 are fixed to an inner face 40 of the rear face plate 22B. Further, a substrate 42 is fixed to the inner face 40 of the rear face plate 22B. This substrate 42 is the one which has, for example, a function of distributing DC power source to the plurality of electronic circuits. A cable 44 is installed between the substrate 42 and the power source circuit. Incidentally, one or a plurality of conductive wire(s) is included in each cable. The plurality of conductive wires may configure a twisted cable.

In the internal AC wiring unit 34, internal AC wiring 46 is installed in the shield case 38. In the illustrated configuration example, an inlet 48, a plurality of connectors 50, 52, 54, a relay substrate 56, a plurality of internal AC cables 60, 62, 64, 66, 68 are included in the internal AC wiring 46. A main power source switch is connected to the connector 50. The internal AC cable 60 is installed between the connector 50 and the inlet 48. A connector 58 is installed on the relay substrate 56. The internal AC cable 62 is installed between the connector 50 and the connector 58. The internal AC cable 66 is installed between the connector 58 and the connector 52. The internal AC cable 68 is installed between the connector 58 and the connector 54.

In the illustrated configuration example, an AC socket array is connected to the connector 52 via an insulation transformer. The AC socket array is the one which supplies AC power to the plurality of pieces of optional equipment. A jelly warmer is connected to the connector 54 as the optional equipment. The jelly warmer is a device which warms jelly which acts as an acoustic propagation medium. The internal AC cable 64 which is pulled out of the connector 58 is connected to the power source circuit. The relay substrate 56 is the one which functions as a distribution substrate or a terminal block and a conductive pattern for distribution of the AC power is formed on the relay substrate 56. Other functions may be added to the relay substrate 56. For example, a switch which turns on and off supply of the AC power to external equipment may be installed on the relay substrate 56. In addition, an electronic circuit such as a noise filter and so forth may be installed thereon.

The shield case 36 is installed on the inner face 40 of the rear face plate 22B, shifting upward and shifting in a+x direction, and the shield case 38 is installed on the inner face 40 of the rear face plate 22B, shifting downward in a−x direction. Overlapping does not occur between the two shield cases 36, 38 in the z-direction. The shield case 36 has a lower face plate 36A and an opening 70 is formed in the lower face plate 36A at a position which deviates in the −x-direction. The shield case 38 has an upper face plate 38A and an opening 72 is famed in the upper face plate 38A at a position which deviates in the +x direction.

The lower face plate 36A and the upper face plate 38A are in a parallel relation, and a gap between them is, for example, about 5 to 10 mm. That is, both are in a mutually close positional relation. The opening 70 and the opening 72 are in a partially overlapping positional relation when viewing from the z direction. The opening 72 is an outlet opening which ejects the internal AC cable 64, and the opening 70 is an inlet opening which accepts the internal AC cable 64. The internal AC cable 64 is composed of a section which is accommodated in the shield case 38, a section which is accommodated in the shield case 36, and an exposed section between them. Since the two openings are close to each other, a length of the exposed section is short, and induction of the noise in the exposed section causes almost no problem.

Although radiation of the electromagnetic wave could occur in the power source circuit, the electromagnetic wave is locally trapped in the shield case 36. That the electromagnetic wave reaches the respective electronic circuits in the casing and the internal AC wiring 46 is effectively prevented. In a case where conductive noise which is conducted through the internal AC cable 64 becomes a problem, a noise filter may be installed on the internal AC cable 64. The noise filter is configured by an electronic filter circuit, a ferrite coil and so forth.

According to the shield structure pertaining to the embodiment, since the internal AC wiring 46 which has been conventionally naked is accommodated in the shield case 38, the internal AC wiring 46 can be protected from the radiation noise, and it becomes possible to effectively reduce the noise which leaks to the outside. For example, in a case of taking measures against the noise by installing the noise filters such as the ferrite coils and so forth on the individual internal AC cables, the problem of cost-rising inevitably occurs. However, according to the embodiment, the noise can be effectively suppressed by a very simple configuration. Nevertheless, the conventionally used noise filter may be used in combination with the shield structure pertaining to the embodiment.

Figure 3:
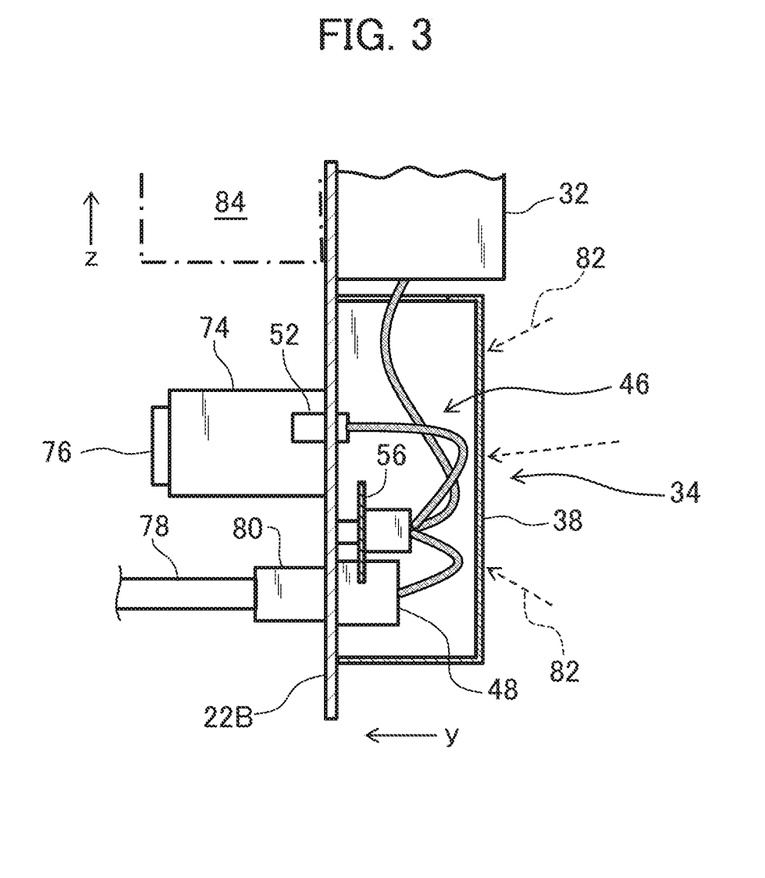
FIG. 3 is a sectional diagram of an AC internal wiring unit.

A section of the internal AC wiring unit 34 is illustrated in FIG. 3. The same signs are assigned to the already described elements and description thereof is omitted. The same applies to descriptions in FIG. 4 and subsequent respective drawings.

The shield case 38 is directly fixed to the rear face plate 22B with a not illustrated plurality of screws and so forth. A plug 80 which is installed on an end of an external AC cable 78 is inserted into the inlet 48. The connector 52 is installed in a state of passing through the rear face plate 22B. Other connectors which are not illustrated in FIG. 3 are also arranged similarly. A pedestal 74 is installed in the form of protruding from an outer face of the rear face plate 22B in the y direction, and a main power source switch 76 is installed on an end thereof. The main power source switch 76 appears outside through an opening which is provided in a covering panel which acts as a decorative plate. An insulation transformer 84 and so forth are installed on an outer face of the rear face plate 22B as necessary. Besides this, also, the AC socket array is installed on the outer face of the rear face plate 22B as necessary. Radiation noise 82 which is present in the casing is blocked out by the shield case 38, and the internal AC wiring 46 is protected from the radiation noise 82.

It is also conceivable to configure one box-shaped shield case by integrating the shield case 36 with the shield case 38. However, in that case, the possibility that influence of the electromagnetic wave which is generated in the power source circuit would become liable to exert on the internal AC wiring 46 and, as a result, the noise which leaks to the external AC cable 78 and so forth would become large can be pointed out. In contrast, occurrence of the above-mentioned problem can be avoided by installing the two shield cases which individually shield the power source circuit and the internal AC wiring 46.

In addition, according to the embodiment, since the internal AC wiring 46 is wrapped up by the shield case 38, it can be physically protected. In particular, when attaching a panel which configures the casing, nipping of the internal AC cable can be effectively prevented. According to the embodiment, since it becomes also possible to bring each electronic circuit close to a power source system, miniaturization of the casing can be promoted in that case.

Incidentally, in a case where the internal AC wiring 46 is naked, such instability that an amount and a characteristic of the noise which leaks change depending on postures of the plurality of internal AC cables occurs. However, according to the above-mentioned configuration, such instability can be solved. This is a major advantage in designing and manufacturing the ultrasonic diagnostic apparatus.

Figure 4:
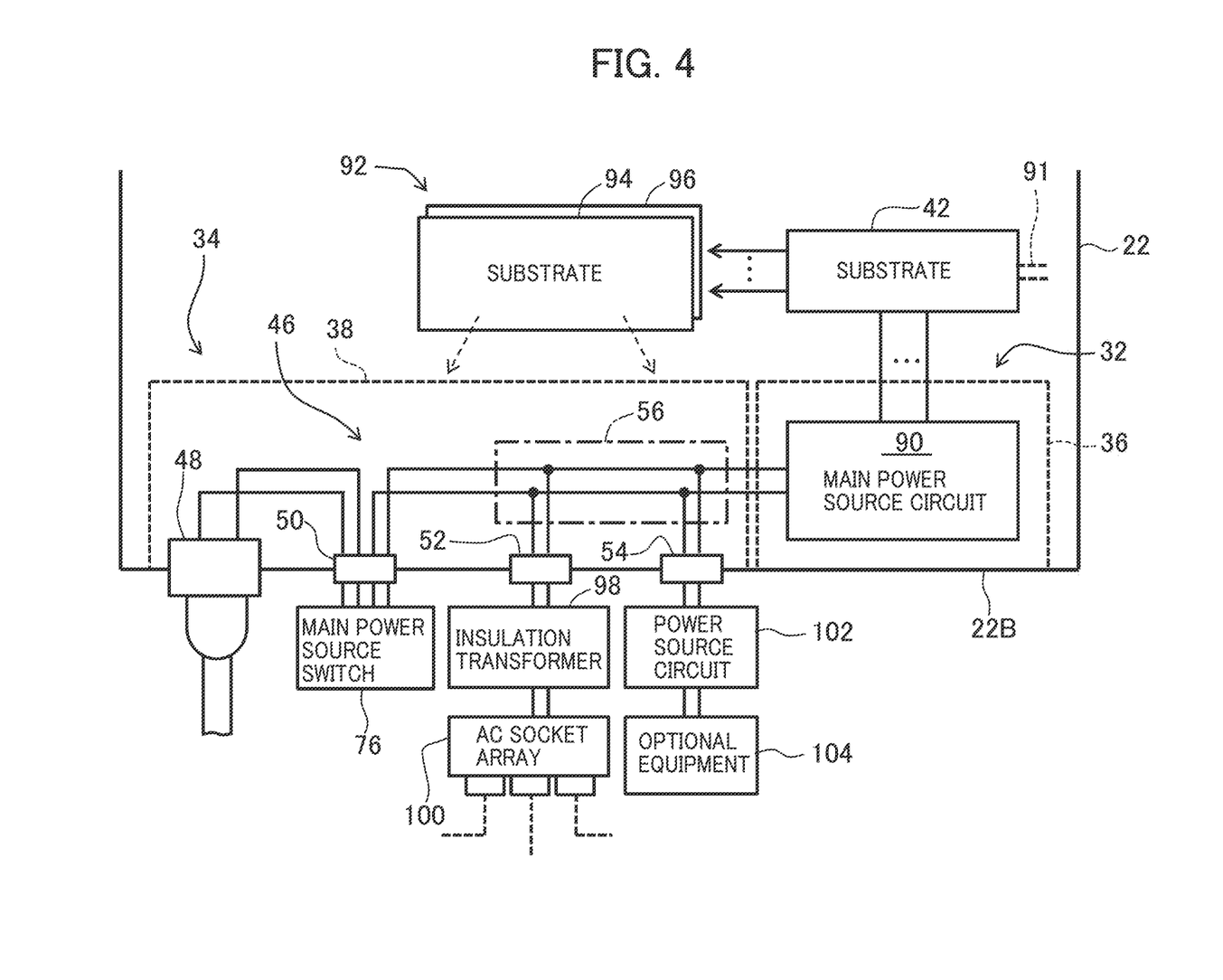
FIG. 4 is a power-source-related circuit diagram.

A power-source-related circuit diagram is illustrated in FIG. 4. In FIG. 4, also, the two shield cases 36, 38 which are installed in the casing 22 are illustrated. The substrate 42 is connected to a main power source circuit 90 and the DC power is supplied to respective substrates 94, 96 via the substrate 42. As already described, the electronic circuits, the signal lines and so forth on the respective substrates 94, 96 would become the noise sources. Also, wiring between the substrates would become the noise source. The radiation noise which is generated in them is blocked out by the shield case 38.

A plurality of AC power line pairs are connected in parallel with one another via the relay substrate 56. The inlet 48, and the plurality of connectors 50, 52, 54 are attached to the rear face plate 22B of the casing 22. In the illustrated configuration example, the main power source switch 76 is connected to the connector 50. An AC socket array 100 is connected to the connector 52 via an insulation transformer 98. The AC socket array 100 is configured by a plurality of sockets and the plug which is installed on the end of the external AC cable which extends from optional equipment is inserted into each of the individual sockets. Optional equipment 104 is connected to the connector 54 via a power source circuit 102. The optional equipment 104 is, for example, a jelly warmer. A recorder, a printer and so forth are given as other pieces of optional equipment. Each of the connectors 50, 52, 54 is configured by the socket and the plug and the socket is attached to the rear face plate.

Incidentally, in the illustrated configuration example, it is possible to connect a DC battery to the substrate 42 (see a sign 91), and in that case, the DC battery is installed on an inner part or an outer part of the casing 22. In a case where the DC battery is arranged on the outer part of the casing 22, it is desirable to take measures against the noise as necessary.

According to the embodiment, since the internal AC wiring 46 is protected by the shield case 38, also the noise which leaks from a power source route of the plurality of pieces of external equipment can be effectively reduced, besides leakage of the noise from the main external AC cable. In particular, according to the embodiment, shield processing can be performed in a lump on a plurality of connection parts to which a plurality of external power source lines are connected and a wiring group which couples together them by a simple configuration.

Figure 5:
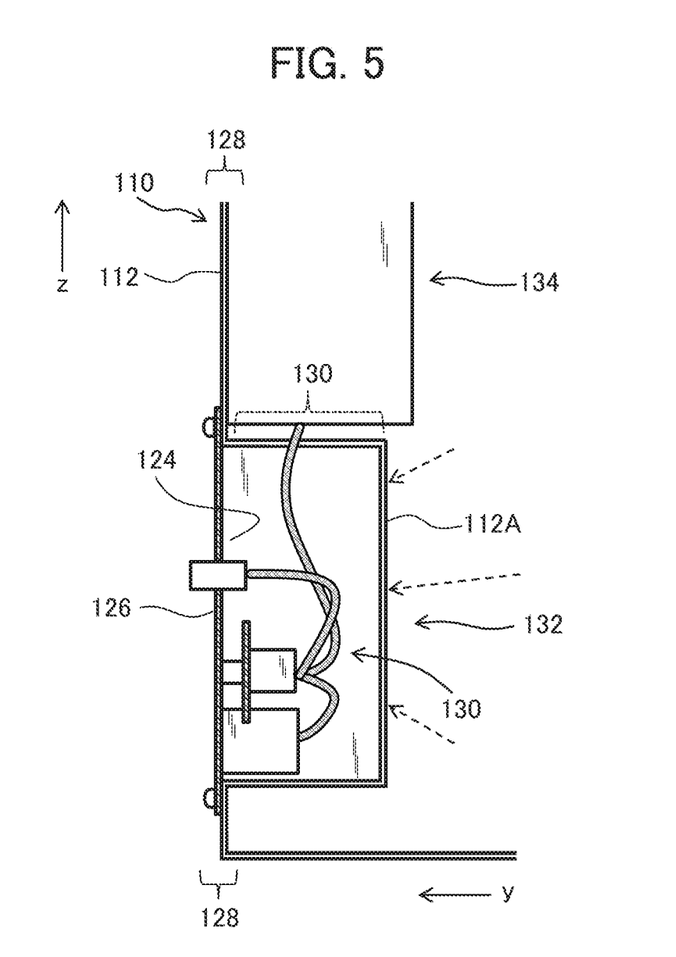
FIG. 5 is a diagram illustrating a second practical example of the shield structure.

A second practical example of the shield structure pertaining to the embodiment is illustrated in FIG. 5. A shield case 112A is configured by performing processing on a lower part of a rear face plate 112 of a casing 110. The shield case 112A can be practically regarded as part of the casing 110. The shield case 112A has a rectangular opening which faces the +y direction and the opening is covered with a cover 126. The cover 126 is configured by a metal member.

As designated by the sign 128, parts which function as an outer shield case are parts of the rear face plate 112 other than the shield case 112A, and the cover 126. As designated by the sign 130, the shield case 112A functions as a second inner shield case. A power source unit 134 has a configuration which is the same as the configuration illustrated in FIG. 2 and so forth. Also, in the second practical example, since the internal AC wiring 130 is wrapped with the shield case 112A in an internal AC wiring unit 132, the internal AC wiring 130 is protected from the radiation noise which is generated in the casing 110.

Incidentally, although, in the configuration illustrated in FIG. 5, a plurality of parts which configure the internal AC wiring 130 are attached to an inner face of the cover 126, these components may be attached to an outer face of the shield case 112A.

Figure 6:
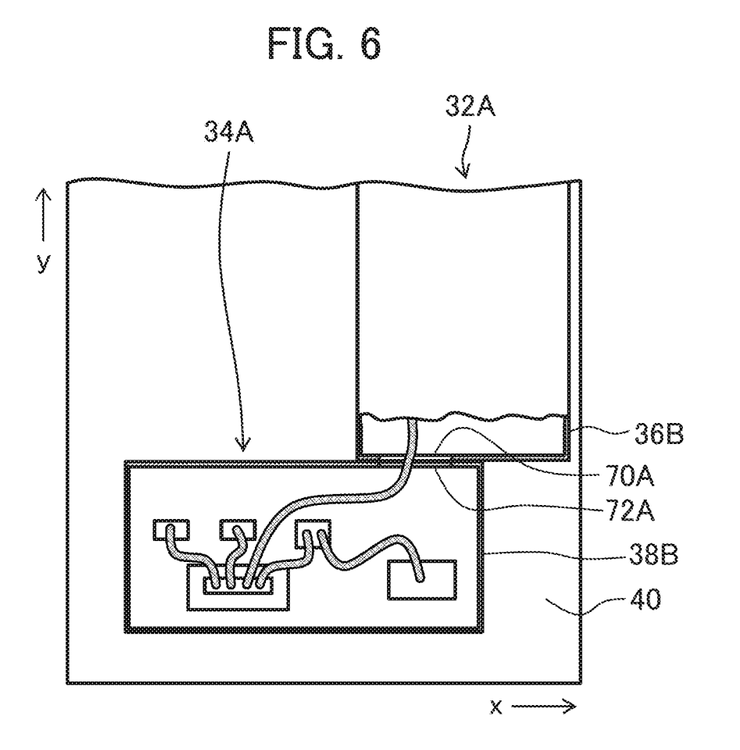
FIG. 6 is a diagram illustrating a third practical example of the shield structure.

A third practical example of the shield structure pertaining to the embodiment is illustrated in FIG. 6. A power source unit 32A and an internal AC wiring unit 34A are installed on the inner face 40 of the rear face plate. Those units 32A, 34A are physically in contact with each other or are coupled together. A shield case 36B and a shield case 38B are coupled together, and a gap is not present between them, looking at them substantially. An opening 70A and an opening 72A match each other in a horizontal direction, and the internal AC cable is inserted into and passes through those openings 70A, 72A. According to this configuration, since the internal AC cable is not exposed between the two units, it becomes possible to more effectively prevent intrusion of the noise thereinto.

Incidentally, arrangement of the power source unit and the internal AC unit may be reversed in an up-down direction. Any of the units may be attached other than the rear face plate. Nevertheless, workability becomes favorable and it becomes easy to arrange the two units to be close to each other by attaching the two units to the common rear face plate.

The above-described shield structure may be applied to an ultrasonic diagnostic apparatus other than the cart-type ultrasonic diagnostic apparatus. For example, it may be applied to a portable type ultrasonic diagnostic apparatus. Incidentally, it is also conceivable to apply the above-described shield structure to other medical apparatuses.

REFERENCE SIGNS LIST

10 ultrasonic diagnostic apparatus, 12 apparatus main body, 14 support mechanism, 16 operation panel, 18 lower part, 22 casing (housing, outer shield case), 32 power source unit, 34 internal AC wiring unit, 36 shield case (first inner shield case), 38 shield case (second inner shield case), 46 internal AC wiring.

The invention claimed is:

1. An ultrasonic diagnostic apparatus including:
   a housing which is structured as an outer shield case;
   a first inner shield case installed in the housing and accommodating a power source circuit, the power source circuit configured to power an electronic circuit which functions in an ultrasonic diagnosis; and
   a second inner shield case structured as a shield case which is different from the first inner shield case, the second inner shield case installed in the housing and accommodating internal AC wiring which is installed on the input side of the power source circuit,
   wherein the internal AC wiring includes:
   a relay substrate,
   a first internal AC cable which is installed between an external AC cable and the relay substrate, and
   a second internal AC cable which is installed between the relay substrate and the power source circuit.

2. The ultrasonic diagnostic apparatus according to claim 1, wherein
   the internal AC wiring further includes a third internal AC cable which is installed between the relay substrate and a power source connector for external equipment.

3. An ultrasonic diagnostic apparatus including:
   a housing which is structured as an outer shield case;
   a first inner shield case installed in the housing and accommodating a power source circuit, the power source circuit configured to power an electronic circuit which functions in an ultrasonic diagnosis; and
   a second inner shield case structured as a shield case which is different from the first inner shield case, the second inner shield case installed in the housing and accommodating internal AC wiring which is installed on the input side of the power source circuit,
   the internal AC wiring includes an internal AC cable configured to supply the power to the power source circuit,
   the first inner shield case has a first side face having a first opening configured to accept the internal AC cable,
   the second inner shield case has a second side face having a second opening configured to eject the internal AC cable, and
   the first side face and the second side face mutually face.

4. The ultrasonic diagnostic apparatus according to claim 3, wherein
   the first opening and the second opening are close to each other, and the first opening and the second opening are in a positional relation such that they at least partially overlap when viewing from a direction which is orthogonal to the first side face and the second side face.

5. An ultrasonic diagnostic apparatus including:
   a housing which is structured as an outer shield case;
   a first inner shield case installed in the housing and accommodating a power source circuit, the power source circuit configured to power an electronic circuit which functions in an ultrasonic diagnosis; and a second inner shield case structured as a shield case which is different from the first inner shield case, the second inner shield case installed in the housing and accommodating internal AC wiring which is installed on the input side of the power source circuit, wherein the housing includes:

a front face plate equipped with a probe connector, and a rear face plate, wherein a digital electronic circuit, an analog electronic circuit, the power source circuit, and the internal AC wiring are accommodated in an internal space between the front face plate and the rear face plate, and wherein the first inner shield case and the second inner shield case are fixed to an inner face of the rear face plate.

* * * * *